United States Patent [19]

Campbell et al.

[11] Patent Number: 5,135,955
[45] Date of Patent: Aug. 4, 1992

[54] PROPANAMINE DERIVATIVES

[75] Inventors: Jack B. Campbell; Gerald F. Smith, both of Indianapolis; William W. Turner, Bloomington, all of Ind.

[73] Assignee: Eli Lilly and Company, Indianapolis, Ind.

[21] Appl. No.: 313,571

[22] Filed: Feb. 22, 1989

Related U.S. Application Data

[63] Continuation-in-part of Ser. No. 185,675, Apr. 25, 1988, abandoned.

[51] Int. Cl.$^5$ ............................................ A61K 31/135
[52] U.S. Cl. .................................... 514/654; 514/649; 514/822
[58] Field of Search ........................ 514/649, 654, 822

[56] References Cited

U.S. PATENT DOCUMENTS

| | | | |
|---|---|---|---|
| 4,391,826 | 7/1983 | Mills et al. | 424/324 |
| 4,721,786 | 1/1988 | Weissmuller et al. | 71/88 |
| 4,804,406 | 2/1989 | Weissmuller et al. | 71/121 |
| 4,845,127 | 7/1989 | Mills et al. | 514/539 |
| 4,876,282 | 10/1989 | Robertson et al. | 514/554 |
| 4,996,235 | 2/1991 | Robertson et al. | 514/649 |

FOREIGN PATENT DOCUMENTS

| | | |
|---|---|---|
| 006766 | 1/1980 | European Pat. Off. . |
| 007204 | 1/1980 | European Pat. Off. . |
| 007205 | 1/1980 | European Pat. Off. . |
| 007206 | 1/1980 | European Pat. Off. . |
| 047536 | 3/1982 | European Pat. Off. . |
| 048037 | 3/1982 | European Pat. Off. . |
| 197798 | 5/1982 | New Zealand . |
| 1591267 | 6/1981 | United Kingdom . |

OTHER PUBLICATIONS

Dokl. Bolg. Akad. Nauk. 20(10):1029-32 (1967).
Drug Treatment for Metastasis of the Lewis Lung Carcinoma: No Correlation Between Inhibition of Lung Metastasis and Survival submitted to *Cancer Research*.
Inhibition of Spontaneous Metasis with a Variety of Antithrombotic Agents Does not Correlate with Survival for talk at 79th Annual Meeting of the American Association for Cancer Research (1983).

*Primary Examiner*—Frederick E. Waddell
*Assistant Examiner*—K. Weddington
*Attorney, Agent, or Firm*—John C. Demeter; Leroy Whitaker

[57] ABSTRACT

Substituted propanamines having anticoagulant or antifungal activity are disclosed. Also disclosed are methods of use involving the substituted propanamines as well as pharmaceutical compositions containing them.

7 Claims, No Drawings

PROPANAMINE DERIVATIVES

This application is a continuation-in-part of U.S. Ser. No. 07/185,675 filed Apr. 25, 1988, now abandoned.

BACKGROUND OF THE INVENTION

The present invention provides substituted propanamine derivatives exhibiting antifungal activity, anticoagulant activity or both. The need for adequate antifungal therapy to combat opportunistic pathogens has been, and continues to be, a fertile area of research. Similarly, compounds exhibiting anticoagulant activity in humans find utility in a variety of clinical settings including treatment of myocardial infarction, pulmonary embolism, cerebrovascular disease and the like. Some anticoagulant agents have also been reported as having anticancer activity. The present invention provides a new class of compounds which find utility as antifungal agents, anticoaguant agents or both.

SUMMARY OF THE INVENTION

The present invention is directed to a compound of the formula $$R^1-CH_2-\underset{\underset{R^2}{|}}{CH}-\underset{\underset{R^3}{|}}{CH}-NR^4R^5 \quad (I)$$

and pharmaceutically acceptable salts thereof wherein: $R^1$ is naphthyl, $C_1-C_4$ alkoxy-substituted naphthyl,

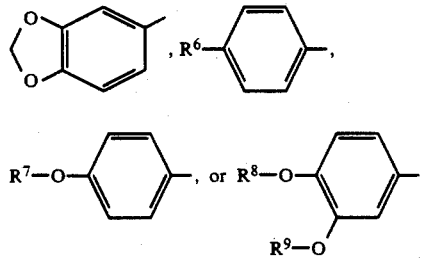

wherein $R^6$ is $C_1-C_4$ alkyl, trihalomethyl, phenyl or $-NR^{10}R^{11}$, where $R^{10}$ and $R^{11}$ are each independently hydrogen or $C_1-C_4$ alkyl; $R^7$ is $C_1-C_{14}$ alkyl, $C_3-C_6$ cycloalkyl-$(CH_2)_m$-, $R^{12}-X-R^{13}$, $-(C_1-C_4$ alkyl)-$C\equiv N$,

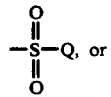

$-(CH_2)_n-Z$, wherein m is an integer from 0 to 3, both inclusive; n is an integer from 1 to 4, both inclusive; X is —O— or —S—; $R^{12}$ and $R^{13}$ are each $C_1-C_4$ alkyl; Q is phenyl or $C_1-C_4$ alkyl; and Z is $NR^{10}R^{11}$ where $R^{10}$ and $R^{11}$ are as defined above, or Z is $C_3-C_6$ cycloalkyl, naphthyl, pyridinyl, imidazolyl, triazolyl, phenyl or phenyl substituted with one or two groups selected from halo, trihalomethyl or $C_1-C_4$ alkoxy; $R^8$ is $C_3-C_6$ cycloalkyl-$(CH_2)_m$—; $R^9$ is $C_1-C_4$ alkyl;

$R^2$ is hydrogen, phenyl, halo-substituted phenyl, biphenyl, naphthyl, pyridinyl,

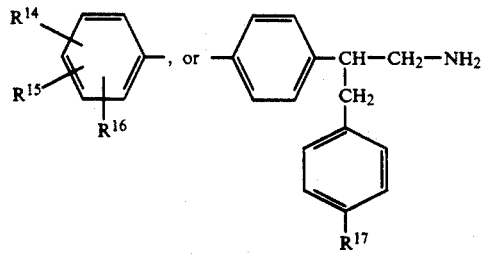

wherein $R^{14}$, $R^{15}$ and $R^{16}$ are each independently hydrogen or $C_1-C_4$ alkoxy and $R^{17}$ is $C_5-C_8$ alkoxy; $R^3$ is hydrogen, $C_1-C_8$ alkyl, or $C_3-C_6$ cycloalkyl; and $R^4$ and $R^5$ are each independently hydrogen, $C_1-C_6$ alkyl, trihalomethyl-substituted cyclohexyl, $-(CH_2)_n-NR^{10}R^{11}$, wherein n, $R^{10}$ and $R^{11}$ are as defined above or, additionally, $R^{10}$ and $R^{11}$ taken together with the nitrogen atom to which they are attached form a morpholinyl group; or $R^4$ and $R^5$ taken together with the nitrogen atom to which they are attached form a pyrrolidinyl, imidazolyl or morpholinyl group, said morpholinyl group optionally substituted with one or two $C_1-C_4$ alkyl groups.

Also disclosed and claimed is a method of inhibiting the coagulation of blood in a patient in need thereof by administering to said patient an effective anticoagulant amount of a compound of formula I as defined above or a pharmaceutically acceptable salt thereof. The present invention also provides a method of preventing or treating a fungal infection in a patient in need thereof by administering to said patient an effective antifungal amount of a compound of formula I as defined above or a pharmaceutically acceptable salt thereof. Similarly, pharmaceutical compositions are provided including an effective amount of a compound of formula I as defined above or a pharmaceutically acceptable salt thereof in association with one or more pharmaceutically acceptable carriers.

DETAILED DESCRIPTION OF THE INVENTION

As used herein, the terms "$C_1-C_4$ alkoxy" and "$C_5-C_8$ alkoxy" refer to straight or branched chain alkoxy radicals of 1 to 4 carbon atoms inclusive and 5 to 8 carbon atoms inclusive, respectively. Examples of such radicals include methoxy, ethoxy, n-propoxy, isopropoxy, n-butoxy, pentoxy, hexoxy, heptoxy, isoheptoxy, sec-heptoxy and the like. Thus, as used herein the term "$C_1-C_4$ alkoxy-substituted naphthyl" means a naphthyl moiety substituted with a $C_1-C_4$ alkoxy radical as that term is defined above.

As used herein, the term "$C_1-C_{14}$ alkyl" refers to straight or branched chain aliphatic radicals of 1 to 14 carbon atoms, inclusive such as methyl, ethyl, propyl, isopropyl, butyl, sec-butyl, tert-butyl, amyl, isoamyl, hexyl, sec-hexyl, heptyl, 2,2-dimethylpentyl, octyl, isooctyl, sec-octyl, nonyl, 1-, 2-, 3-, 4-, 5-, 6-, 7-, or 8-methylnonyl, 1-, 2-, 3-, 4-, 5-, or 6-ethyloctyl, undecyl, dodecyl, tridecyl, tetradecyl and the like. The term "$C_1-C_{14}$ alkyl" includes within its definition the term "$C_1-C_4$ alkyl" and the term "$C_1-C_8$ alkyl".

As used herein, the term "$C_3-C_6$ cycloalkyl" refers to saturated alicyclic rings of 3 to 6 carbon atoms, both inclusive, such as cyclopropyl, methycyclopropyl, cyclobutyl, cycopentyl, cyclohexyl and the like.

As used herein, the term "halo" refers to fluoro, chloro, bromo and iodo. Accordingly, the term "halo-substituted phenyl" refers to a phenyl moiety substituted with one or more fluoro, chloro, bromo or iodo atoms. Similarly, the term "trihalomethyl" refers to radicals such as trifluoromethyl, trichloromethyl, tribromomethyl and triiodomethyl.

The pharmaceutically acceptable salts of the present invention are acid addition salts derived from inorganic acids such as hydrochloric, phosphoric, phosphorous, nitric, sulfuric, hydrobromic, hydriodic acid and the like. Additionally, such salts may be derived from organic acids such as aliphatic mono and dicarboxylic acids, phenyl-substituted alkanoic acids, hydroxyalkanoic and alkandioic acids, for example. Therefore, such pharmaceutically acceptable salts include sulfate, bisulfate, chloride, bromide, iodide, fluoride, nitrate, phosphate, acetate, formate, propionate, caprate, fumarate, maleate, benzoate, chlorobenzoate, methylbenzoate, dinitrobenzoate, hydroxybenzoate, phthalate, benzenesulfonate, phenylacetate, phenylpropionate, citrate, malate, tartrate, and the like. Salts from inorganic acids are preferred, particularly the hydrochloride salt.

Preferred compounds of the present invention are those compounds of formula I wherein $R^1$ is

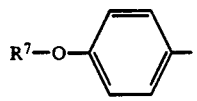

wherein $R^7$ is $C_1$-$C_{14}$ alkyl or —$(CH_2)_nZ$, where n and Z are as defined above; $R^2$ is hydrogen, phenyl or naphthyl; and $R^3$, $R^4$ and $R^5$ are hydrogen or $C_1$-$C_4$ alkyl, and pharmaceutically acceptable salts thereof. Of the above group of preferred compounds, those compounds which are particularly preferred are those wherein $R^7$ is $C_3$-$C_{10}$ alkyl or, when $R^7$ is —$(CH_2)_nZ$, n is 1 or 2 and Z is phenyl; and $R^2$ is hydrogen or phenyl, and pharmaceutically acceptable salts thereof. Of the above group of particularly preferred compounds, those compounds which are most particularly preferred are those wherein $R^7$ is $C_4$-$C_7$ alkyl and pharmaceutically acceptable salts thereof.

The compounds of the present invention are readily prepared by known methodologies using starting materials which are either commercially available or otherwise prepared by conventional techniques. For example, the compounds of formula 1 wherein $R^3$ is hydrogen (i.e., the β-substituted propanamines) may be prepared by condensing an $R^1$-substituted aldehyde of the formula

     (II)

with an appropriate $R^2$-substituted nitrile of the formula $R^2$—$CH_2$—CN     (III)

to form an intermediate nitrile of the formula

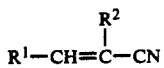     (IV)

where the values for $R^1$ and $R^2$ are as defined in formula I, above. The reaction between the above-aldehyde and nitrile is usually performed in equimolar amounts although ratios other than equimolar are completely operative. Said reaction is carried out in an inert organic solvent, preferably an alcoholic solvent such as methanol in the presence of base. The base employed may be inorganic or organic in nature and is preferably an alkali metal hydroxide. The reaction mixture is typically stirred and the temperature maintained anywhere from about ambient temperature up to the boiling point of the solvent for a time sufficient to effect formation of said intermediate nitrile (IV). The skilled artisan will readily appreciate that at temperatures in excess of ambient, the amount of time required to form said intermediate will likely be reduced, although stirring at room temperature for about eight to twelve hours is totally operative. Upon completion of the reaction and the addition of water, the resultant solid intermediate nitrile IV is collected, washed and reduced to the primary amine (i.e., those compounds of formula I wherein $R^4$ and $R^5$ are is hydrogen). The reduction is effected as by the catalytic action of platinum, palladium or preferably Raney nickel in a hydrogen atmosphere in the presence of anhydrous ammonia. The solvent used is a nonreactive solvent such as tetrahydrofuran or an alcoholic solvent such as methanol or ethanol. The reaction is carried out at elevated temperatures of from about 50° to about 200° centigrade (C) and pressures of from about 50 to about 2000 pounds per square inch (psi). The reaction is allowed to continue for a time sufficient to allow substantial completion of the reaction, typically from about 5 to about 15 hours. Such reaction conditions are completely operative but should not be construed as being the exclusive means of reducing the intermediate nitrile IV, the reduction itself being conventional in the art. Isolation and work-up of the resultant product is similarly conventional, for example, by removal of the catalyst and solvent, resuspension and filtration through magnesia-silica gel and subsequent recrystallization from an appropriate organic solvent as needed.

Those compounds of formula I wherein $R^4$ and $R^5$ are other than hydrogen ($R^3$=hydrogen) are conveniently prepared by catalytically reducing the intermediate nitrile (IV) as described above in the presence of an amine of the formula $NHR^4R^5$     (V)

wherein $R^4$ and $R^5$ are as defined for formula I, above rather than anhydrous ammonia. Subsequent reaction conditions and work-up are substantially the same as described above and render the desired amine.

Those compounds of formula I wherein $R^2$ is hydrogen (i.e., the α-substituted propanamines) are readily prepared by the reductive amination of a ketone of the formula

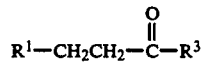     (VI)

wherein $R^1$ and $R^3$ are as defined in formula I, above. Said ketones are either commercially available or may be prepared as described hereinafter. The reductive amination is similarly accomplished by conventional methodology as by the treatment of said ketone with the appropriately substituted amine of the formula $NHR^4R^5$     (VII)

(where R⁴ and R⁵ are as defined in formula I, above) in a nonreactive solvent such as tetrahydrofuran or preferably an alcoholic solvent such as methanol or ethanol. The reduction is effected by the catalytic action of a platinum or palladium catalyst in a hydrogen atmosphere in the presence of the amine (VII). The reaction is carried out at elevated temperatures of from about 50° C. to about 200° C. and at pressures of from about 50 to about 2000 psi. Work-up of the desired product is similarly conventional as will be described hereinafter. The skilled artisan will appreciate that when the value R¹ in ketone VI is

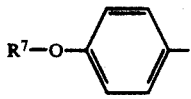

and R⁷ is C₁–C₁₄ alkyl or C₃–C₆ cycloalkyl, alkylation of the phenoxy ketone may be effected either prior to or after the reductive amination utilizing potassium t-butoxide and the appropriate alkyl halide or tosylate under conventional alkylation conditions as described hereinafter.

Compounds of formula which are α, β-substituted are prepared by the condensation of a R¹-containing aldehyde as defined by formula II with an R², R³-substituted ketone according to the following reaction scheme:

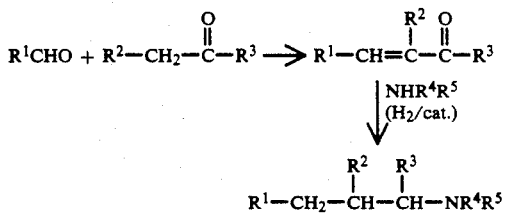

where each of R¹, R², R³, R⁴ and R⁵ are as defined in formula I, above. Approximately equimolar amounts of the aldehyde and ketone are added to a nonreactive organic solvent, preferably toluene, in the presence of a minor amount of a catalyst such as piperidine. The reaction mixture is heated at reflux temperature for a time sufficient to effect condensation, typically from about 4 to about 12 hours. Reductive amination of the resulting ketone is achieved as described previously with the appropriately substituted ketone of formula VII to render the desired α, β-substituted compounds of formula I.

The following illustrates compounds contemplated within the scope of the present invention:

4-(Hexyloxy)-α-methylbenzenepropanamine, hydrochloride
α-Methyl-4-(octyloxy)benzenepropanamine, hydrochloride
α-Methyl-4-(nonyloxy)benzenepropanamine, hydrochloride
N'-[3-4-(Decyloxy)phenyl]-1-methylpropyl]-N,N-dimethyl-1,3-propanediamine dihydrochloride
N-[1-Methyl-3-[4-(nonyloxy)phenyl]propyl]-4-morpholinepropanamine dihydrochloride
N'-[3-[4-(Decyloxy)phenyl]-1-methylpropyl]-N,N-dimethyl-1,2-ethanediamine dihydrochloride
N'-[3-[4-(Dodecyloxy)phenyl]-1-methylpropyl]-N,N-dimethyl-1,3-propanamine dihydrochloride
N-[1-Methyl-3-[4-(tetradecyloxy)phenyl]propyl]-4-morpholinepropanamine dihydrochloride
N,N-Dimethyl-N'-[1-methyl-3-[4-(undecyloxy)phenyl]-propyl]-1,2-ethanediamine dihydrochloride
N-Methyl-N-(1-methylethyl)-N'-(3-phenyl-5-isothiazolyl)urea
N-[3-[4-(Dodecyloxy)phenyl]-1-methylpropyl]-4-morpholineethanamine dihydrochloride
4-(Cyclohexylmethoxy)-α-hexylbenzenepropanamine hydrochloride
α-Cyclohexyl-4-(cyclohexylmethoxy)benzenepropanamine hydrochloride
4-(Cyclohexylmethoxy)-α-methyl-N-[3-(trifluoromethyl)cyclohexyl]benzenepropanamine hydrochloride
4-[3-[4-(Cyclohexylmethoxy)phenyl]-1-ethylpropyl]-morpholine hydrochloride
4-(2-Cyclohexyethoxy)-α-methylbenzenepropanamine hydrochloride
α-Ethyl-4-(octyloxy)benzenepropanamine hydrochloride 4-[3-(Dimethylamino)butyl]phenol hydrochloride
4-Methoxy-N,N,α-trimethylbenzenepropanamine hydrochloride
4-Ethoxy-N,N,α-trimethylbenzenepropanamine hydrochloride
N,N,α-Trimethyl-4-propoxybenzenepropanamine hydrochloride
N,N,α-Trimethyl-4-(pentyloxy)benzenepropanamine hydrochloride
4-(Hexyloxy)-N,N,α-trimethylbenzenepropanamine hydrochloride
4-(Heptyloxy)-N,N,α-trimethylbenzenepropanamine hydrochloride
N,N,α-Trimethyl-4-(3-methylbutoxy)benzenepropanamine hydrochloride
N,N,α-Trimethyl-4-(2-propenyloxy)benzenepropanamine hydrochloride
4-[2-(1,1-Dimethylethoxy)ethoxy]-N,N,α-trimethylbenzenepropanamine hydrochloride
N,N,α-Trimethyl-4-(phenylmethoxy)benzenepropanamine hydrochloride
4-(Cyclohexylmethoxy)-N,N,α-trimethylbenzenepropanmine hydrochloride
4-(2-Cyclohexylethoxy)-N,N,α-trimethylbenzenepropanamine hydrochloride
N,N,α-Trimethyl-4-[(2-fluorophenyl)methoxy-]benzenepropanamine
N,N,α-Trimethyl-4-[(2,4-difluorophenyl)-methoxy]benzenepropanamine hydrochloride
N,N,α-Trimethyl-4-[(3,4-difluorophenyl)-methoxy]benzenepropanamine hydrochloride
N,N,α-Trimethyl-4-[(4-chlorophenyl)methoxy-]benzenepropanamine hydrochloride
N,N,α-Trimethyl-4-(3,4-dichlorophenyl)methoxy]benzenepropanamine hydrochloride
N,N,α-Trimethyl-4-[(4-methoxyphenyl)methoxy]benzenepropanamine hydrochloride
N,α-Dimethyl-4-butoxybenzenepropanamine hydrochloride
N-(1-methylethyl)-α-methyl-4-butoxybenzenepropanamine hydrochloride
4-Butoxy-N,α-dimethyl-N-(1-methylethyl)-benzenepropanamine
N-[3-(4-Butoxyphenyl)-1-methylpropyl]-N,N-dimethyl-1,3-propanediamine dihydrochloride
4-Butoxy-α-methyl-N-(phenylmethyl)benzenepropanamine hydrochloride
4-Butoxy-N,α-dimethyl-N-(phenylmethyl)benzenepropanamine 4-Butoxy-N,N-dimethylbenzenepropanamine hydrochloride These and other aspects of the present invention will be more fully illustrated by reference to the following examples which are not to be construed as a limitation thereon.

EXAMPLE 1

4-(Hexyloxy)-β-phenylbenzenepropanamine

A solution of 103 grams (g) of 4-hexyloxybenzaldehyde and 58.5 g of phenylacetonitrile in ethanol was stirred at room temperature and aqueous sodium hydroxide (50 percent) was added dropwise. The addition of base was stopped upon formation of a precipitate and the resultant mixture was stirred overnight at room temperature. The precipitate was then collected by filtration and washed with water to yield 135 g (88 percent yield) of the intermediate, α-[[4-(hexyloxy)phenyl]methylene]benzeacetonitrile which was reduced as follows.

A mixture of 43 g of the above intermediate nitrile, 10 g of Raney nickel, 150 milliliters (ml) of anhydrous ammonia and 300 ml of tetrahydrofuran were stirred at 140° C. for 10 hours at a pressure of 1000 psi. The catalyst and solvent were then removed and the residue was taken up in diethyl ether and then filtered through magnesia-silica gel. The hydrochloride salt was made in the filtrate by the addition of anhydrous hydrochloric acid. The hydrochloride salt was recovered by recrystallization from ethanol to yield 4-(hexyloxy)-β-phenylbenzenepropanamine hydrochloride (35 percent yield), melting point (m.p.) 144°–145° C.

Elemental Analysis: $C_{21}H_{29}NO \cdot HCl$.
Calc: C, 72.49; H, 8.69; N, 4.03; Cl, 10.19.
Found C, 72.61; H, 8.54; N, 4.23; Cl, 10.38.

EXAMPLE 2

4-(Octyloxy)-β-phenylbenzenepropanamine

A solution of 117 g of 4-octyloxybenzaldehyde and 58.5 g of phenylacetonitrile in methanol was stirred at room temperature and aqueous (50 percent) sodium hydroxide was added dropwise. The addition of base was stopped upon formation of a precipitate and the resultant mixture was stirred overnight at room temperature. The mixture was then poured into a large volume of water and fitered to collect the solids which were washed with water to yield the intermediate, α-[[4-(octyloxy)phenyl]methylene]benzeneacetonitrile. 101.5 Grams of this intermediate nitrile, 25 g of Raney nickel, 150 ml of anhydrous ammonia and 200 ml of tetrahydrofuran were stirred at 140° C. for 10 hours at a pressure of 2,000 psi. The catalyst and solvent were then removed and the residue was taken up in diethyl ether and then filtered through magnesia-silica gel. The hydrochloride salt of the title compound was made in the filtrate by the addition of anhydrous hydrochloric acid. The hydrochloride salt was recovered by recrystallization from ethanol to yield 4-(octyloxy)-β-phenylbenzenepropanamine hydrochloride (18 percent yield), m.p. 127°, decomposition (dec.).

Elemental Analysis: $C_{23}H_{33}NO \cdot HCl$.
Calc: C, 73.47; H, 9.12; N, 3.73; O, 4.26; Cl, 9.43.
Found: C, 73.38; H, 8.76; N, 4.09; O, 4.53; Cl, 9.49.

EXAMPLE 3

4-[(2-Ethylhexyl)oxy]-β-phenylbenzenepropanamine hydrochloride

4-Hydroxybenzaldehyde (61 g) and 2-ethylhexylbromide (106 g) were added to 150 ml of dimethylformamide containing 138 g of potassium carbonate. The mixture was refluxed overnight and then poured into a volume of cold water and extracted with ethyl acetate. The extract was dried, evaporated and distilled (0.1 millimeter vacuum) to yield 4-[(2-ethylhexyl)oxy]benzaldehyde, boiling point (b.p.) 118°–121° C.

70.2 Grams of 4-[(2-ethylhexyl)oxy]benzaldehyde (prepared as described in the preceding paragraph) and 38.6 g of phenylacetonitrile were added to 800 ml of methanol and stirred cold (10°–15° C.). To this was added (dropwise) 125 ml of aqueous sodium hydroxide (50 percent) with continued stirring at 10°–15° C. for an additional two hours. The mixture was then stirred overnight at room temperature and then poured into cold water and extracted with ethyl acetate. The extract was dried and evaporated to yield α-[[4-(2-ethylhexyloxy)phenyl]methylene]benzeneacetonitrile which was catalytically reduced as follows.

95.6 Grams of the above nitrile, 25 g of Raney nickel, 150 ml of anhydrous ammonia and 225 ml of tetrahydrofuran were stirred at 140° C. for 12 hours at a pressure of 1500 psi. The catalyst and solvent were then removed and the residual was vacuum distilled to yield (60 percent) 4-[(2-ethylhexyl)oxy]-β-phenylbenzenepropanamine, b.p. 180°–185° C.

Elemental Analysis: $C_{23}H_{33}NO$.
Calc: C, 81.37; H, 9.80; N, 4.13.
Found: C, 81.18; H, 9.61; N, 4.00.

The hydrochloride salt of the title compound was prepared from anhydrous hydrochloric acid to yield a white precipitate which was subsequently recrystallized from ethanol to yield 4-[(2-ethylhexyl)oxy]-β-phenylbenzenepropanamine hydrochloride, m.p. 112°–113° C.

Elemental Analysis: $C_{23}H_{33}NO \cdot HCl$.
Calc: C, 73.47; H, 9.12; N, 3.73.
Found C, 73.72; H, 9.40; N, 3.95.

Utilizing procedures described in Examples 1–3, the following additional compounds were prepared.

EXAMPLE 4

4-(Pentyloxy)-β-phenylbenzenepropanamine hydrochloride

Elemental Analysis: $C_{20}H_{27}NO \cdot HCl$.
Calc: C, 71.94; H, 8.45; N, 4.19.
Found: C, 71.86; H, 8.21; N, 4.09.
m.p. 153°–154° C.

EXAMPLE 5

4-(Heptyloxy)-β-phenylbenzenepropanamine hydrochloride

Elemental Analysis: $C_{22}H_{31}NO \cdot HCl$.
Calc: C, 73.00; H, 8.91; N, 3.87.
Found: C, 73.18; H, 9.08; N, 3.99.
m.p. 130°–132° C.

EXAMPLE 6

4-(Butyloxy)-β-phenylbenzenepropanamine hydrochloride

Elemental Analysis: $C_{19}H_{25}NO \cdot HCl$.
Calc: C, 71.34; H, 8.19; N, 4.38; O, 5.00; Cl, 11.08.

Found: C, 71.11; H, 7.99; N, 4.52; O, 5.22; Cl, 11.38.
m.p. 169° C. (dec.).

EXAMPLE 7

β-Phenyl[1,1'-biphenyl]-4-propanamine hydrochloride

Elemental Analysis: $C_{21}H_{21}N.HCl$.
Calc: C, 77.88; H, 6.85; N, 4.32; Cl, 10.95.
Found: C, 77.71; H, 6.82; N, 4.01; Cl, 10.93.
m.p. 219°–221° C.

EXAMPLE 8

β-(3,4-Dimethoxy)phenyl[1,1'-biphenyl]-4-propanamine hydrochloride

Elemental Analysis: $C_{23}H_{25}NO_2.HCl$.
Calc: C, 71.96; H, 6.83; N, 3.65.
Found: C, 71.77; H, 6.92; N, 3.64.
m.p. 265°–267° C.

EXAMPLE 9

β-(4-Methoxy)phenyl[1,1'-biphenyl]-4-propanamine

Elemental Analysis: $C_{22}H_{23}NO$.
Calc: C, 83.24; H, 7.30; N, 4.41.
Found: C, 83.08; H, 7.24; N, 4.20.
m.p. 108°–109° C.

EXAMPLE 10

β-[[4-(Hexyloxy)phenyl]methyl]-2-naphthaleneethanamine hydrochloride

Elemental Analysis: $C_{25}H_{31}NO.HCl$.
Calc: C, 75.45; H, 8.10; N, 3.52; Cl, 8.91.
Found: C, 75.30; H, 8.29; N, 3.48; Cl, 8.94.
m.p. 123° C. (dec.).

EXAMPLE 11

(±)-β-[[4-(Octyloxy)phenyl]methyl][1,1'-biphenyl-4-ethanamine hydrochloride

Elemental Analysis: $C_{29}H_{37}NO.HCl$.
Calc: C, 77.05; H, 8.47; N, 3.10; O, 3.54; Cl, 7.84.
Found: C, 76.84; H, 8.21; N, 3.07; O, 3.69; C, 7.68.
m.p. 151°–153° C.

EXAMPLE 12

β-[[4-(Pentyloxy)phenyl]methyl][1,1'-biphenyl]-4-ethanamine hydrochloride

Elemental Analysis: $C_{26}H_{31}NO.HCl$.
Calc: C, 76.17; H, 7.84; N, 3.42; O, 3.90; Cl, 8.65.
Found: C, 76.10; H, 8.09; N, 3.42; O, 4.84; Cl, 8.91.
m.p. 189°–191° C.

EXAMPLE 13

β,β'-Bis[[4-(heptyloxy)phenyl]methyl]-1,4-benzenediethanamine dihydrochloride

Elemental Analysis: $C_{38}H_{56}N_2O_2.HCl$
Calc: C, 70.67; H, 9.05; N, 4.34; Cl, 10.98
Found: C, 70.46; H, 8.79; N, 4.59; Cl, 11.00
m.p. >260° C.

EXAMPLE 14

4-(1-Methylethyl)-β-phenylbenzenepropanamine hydrochloride

Elemental Analysis: $C_{18}H_{23}N.HCl$
Calc: C, 74.59; H, 8.35; N, 4.83; Cl, 12.23
Found: C, 74.83; H, 8.63; N, 5.16; Cl, 12.43
m.p. 185°–187° C.

EXAMPLE 15

4-(Pentyloxy)-β-3,4-(dimethoxy)phenylbenzenepropanamine

A solution of 19.2 g of 4-pentoxybenzaldehyde and 17.7 g of 3,4-dimethoxybenzonitrile in methanol was stirred at room temperature while 50 ml of aqueous sodium hydroxide (50 percent) was added. The mixture was stirred overnight at room temperature after which water was added and the resultant solid was collected by filtration, washed with water and dried to yield the intermediate, α-[[4-(pentyloxy)phenyl]methylene]-3,4-acetonitrile. 33.6 Grams of this nitrile, 8 g of Raney nickel, 150 ml anhydrous ammonia, and 300 ml of tetrahydrofuran were stirred at 150° C. for 12 hours at a pressure of 1000 psi. The catalyst and solvent were then removed and the residue was taken up in diethyl ether and then filtered through magnesia-silica gel. The diethyl ether was removed and the residue was placed in acetone (pH adjusted to 12.0). The pH was adjusted to 6.9 using concentrated hydrochloric acid and the precipitate that was present was chilled for about one hour. The solids were collected by filtration and the title compound was recrystallized from ethanol, 227°–228° C.

Elemental Analysis: $C_{22}H_{31}NO_3$.
Calc: C, 67.07; H, 8.19; N, 3.56.
Found: C, 66.88; H, 8.15; N, 3.33.

Utilizing the procedures described in the preceding examples, the following additional compounds were prepared.

EXAMPLE 16

α-(Hexyloxy)-β-(3,4-dimethoxy)phenylbenzenepropanamine hydrochloride

Elemental Analysis: $C_{23}H_{33}NO_3.HCl$.
Calc: C, 67.71; H, 8.40; N, 3.46; C, 8.69.
Found: C, 67.79; H, 8.12; N, 3.61; Cl, 8.48.
m.p. 219°–221° C.

EXAMPLE 17

4-(Octyloxy)-β-(3,4-dimethoxy)phenylbenezenepropanamine hydrochloride

Elemental Analysis: $C_{25}H_{37}NO_3.HCl$.
Calc: C, 68.86; H, 8.78; N, 3.21; C, 8.13.
Found: C, 68.66; H, 9.02; N, 3.43; Cl, 8.15.
m.p. 209°–211° C.

EXAMPLE 18

4-(Octyloxy)-β-(3,4,5-trimethoxy)phenylbenzenepropanamine hydrochloride

Elemental Analysis: $C_{26}H_{39}NO_4.HCl$.
Calc: C, 67.01; H, 8.65; N, 3.01; O, 13.73; Cl, 7.61.
Found: C, 66.90; H, 8.40; N, 2.96; O, 13.63; C, 7.65.
m.p. 173°–174° C.

EXAMPLE 19

4-(Pentyloxy)-β-(2,3,4-trimethoxy)phenylbenzenepropanamine hydrochloride

Elemental Analysis: $C_{23}H_{33}NO_4.HCl$.
Calc: C, 65.16; H, 8.08; N, 3.30; Cl, 8.36.
Found: C, 65.39; H, 7.82; N, 3.09; Cl, 8.57.
m.p. 182°–184° C.

EXAMPLE 20

4-(Heptyloxy)-β-(3,4-dimethoxy)phenylbenzenepropanamine

Elemental Analysis: $C_{24}H_{35}NO_3$.
Calc: C, 68.31; H, 8.60; N, 3.32.
Found: C, 68.36; H, 8.54; N, 3.06.
m.p. 215°–217° C.

EXAMPLE 21

4-(Heptyloxy)-β-(4-methoxy)phenylbenzenepropanamine

Elemental Analysis: $C_{23}H_{33}NO_2$.
Calc: C, 77.70; H, 9.36; N, 3.94.
Found: C, 77.63; H, 9.10; N, 3.72.
m.p. 144° C. (dec.).

EXAMPLE 22

β-Phenyl-1-naphthalenepropanamine hydrochloride

A solution of 46.8 g of 1-naphthaldehyde and 35.1 g of phenylaceotnitrile in 500 ml of methanol was stirred at room temperature and 75 ml of aqueous potassium hydroxide (25 percent) was added. A precipitate formed and the resultant mixture was stirred for an additional hour at room temperature. The precipitate was then collected by filtration and washed with water to yield the intermediate, α-[1-(naphthyl)methylene]-benzeneacetonitrile which was subsequently recrystallized from ethanol to yield long yellow crystals (m.p. 110°–111° C.).

A mixture of 68 g of the above intermediate nitrile, 10 g of Raney nickel, 150 ml of anhydrous ammonia and 270 ml of tetrahydrofuran were stirred at 140° C. for 12 hours at a pressure of 1500 psi. The catalyst and solvent were then removed and the residue was taken up in diethyl ether and then fitered through magnesia-silica gel. The hydrochloride salt was formed in the filtrate by the addition of anhydrous hydrochloric acid. The hydrochloride salt was recovered by recrystallization from ethanol to yield β-phenyl-1-naphthalenepropanamine hydrochloride (71 percent yield),
m.p. 201°–203° C.
Elemental Analysis: $C_{19}H_{19}N.HCl$.
Calc: C, 76.62; H, 6.77; N, 4.70; Cl, 11.90.
Found: C, 76.43; H, 6.90; N, 4.98; Cl, 11.60.

Utilizing the above procedures, the following additional compounds were prepared.

EXAMPLE 23

β(3,4-Dimethoxy)phenyl-1-(4-methoxy)naphthalenepropanamine hydrochloride

Elemental Analysis: $C_{22}H_{25}NO_3.HCl$.
Calc: C, 68.12; H, 6.76; N, 3.61; Cl, 9.14.
Found: C, 68.38; H, 6.67; N, 3.84; Cl, 9.10.
m.p. 256° C. (dec.)

EXAMPLE 24

β-(4-Methoxy)phenyl-1-naphthalenepropanamine

Elemental Analysis: $C_{20}H_{21}NO$.
Calc: C, 73.27; H, 6.76; N, 4.27.
Found: C, 73.01; H, 6.91; N, 4.44.
m.p. 206°–208° C.

EXAMPLE 25

β-(2,3-Dimethoxyphenyl)-2-naphthalenepropanamine

Elemental Analysis: $C_{21}H_{23}NO_2$.

Calc: C, 70.48; H, 6.76; N, 3.91.
Found: c, 70.60; H, 6.73; N, 3.93.
m.p. 233°–234° C.

EXAMPLE 26

4(Hexyloxy)-β-(4-fluorophenyl)benzenepropanamine

A solution of 51.5 g of 4-hexyloxybenzaldehyde and 33.8 g of 4-fluorophenylacetonitrile in methanol was stirred at room temperature and aqueous sodium hydroxide (50 percent) was added dropwise until a precipitate appeared. Water was then added and the solids were collected by filtration to render α-[[4-(hexyloxy)phenyl]methylene]-4-fluorophenylacetonitrile which was reduced as follows. 40.2 g of said nitrile, 10 g of Raney nickel, 150 ml of anhydrous ammonia and 300 ml of tetrahydrofuran were stirred at 110° for 12 hours at a pressure of 2000 psi. The catalyst and solvent were removed and the hydrochloride salt was made in the filtrate by the addition of anhydrous hydrochloric acid. Recrystallization from methanol rendered the title compound (20 percent yield).

Elemental Analysis: $C_{21}H_{28}FNO$.
Calc: C, 68.93; H, 7.99; N, 3.83; F, 5.19.
Found: C, 68.80; H, 8.19; N, 3.83; F, 5.38.
m.p. 138°–139° C.

EXAMPLE 27

β-[[(4-Hexyloxy)phenyl]methyl]-3-pyridineethanamine dihydrochloride

To a stirring solution of 20.6 g of 4-hexyloxybenzaldehyde and 11.8 g of 3-pyridylacetonitrile in methanol was added 25 ml of aqueous potassium hydroxide (25 percent). A precipitate formed and the resultant mixture was stirred at room temperature for an additional two hours. The resultant precipitate was collected by filtration, washed with water and recrystallized from ethanol to yield the intermediate, α-[[4-(hexyloxy)phenyl]methylene]-3-pyridylacetonitrile (m.p. 67°–68° C). 46 g of said nitrile, 10 g of Raney nickel, 150 ml of anhydrous ammonia and 300 ml of tetrahydrofuran were stirred at 100° C. for ten hours at a pressure of 1500 psi. The catalyst and solvent were removed and the residue was taken up in diethyl ether and fitered through magnesia-silica gel. The hydrochloride salt was made in the filtrate by the addition of anhydrous hydrochloric acid. Recrystallization from ethanol yielded β-[[4-(hexyloxy)phenyl]methyl]-3-pyridineethanamine dihydrochloride.

Elemental Analysis: $C_{20}H_{28}N_2O.2HCl$.
Calc: C, 62.33; H, 7.85; N, 7.27; Cl, 18.40.
Found: C, 62.06; H, 7.58; N, 7.25; Cl, 18.40.

EXAMPLE 28

N-Ethyl-4-(hexyloxy)-β-phenylbenzenepropanamine

A solution of 103 g of 4-hexyloxybenzaldehyde and 58.5 g of phenylacetonitrile was stirred at room temperature in ethanol with the dropwise addition of a solution of aqueous sodium hydroxide (50 percent). Upon formation of a precipitate, addition of the base was ceased and the resultant mixture was stirred overnight at room temperature. The solids were then collected and washed with water to yield 135 g (88 percent) of the desired intermediate, α-[[4-(hexyloxy)phenyl]methylene]benzeneacetonitrile. 43 Grams of the nitrile, 10 g of palladium catalyst (5 percent), 150 ml of anhydrous ethylamine in 300 ml of a 1:1 mixture of tetrahydrofuran and ethanol were stirred at 120° C. for 12 hours at a pressure of 1500 psi. The catalyst and solvent were then removed and the residue was taken up in diethyl ether and filtered through magnesia-silica gel. The hydrochloride salt was made by the addition of anhydrous hydrochloric acid to the filtrate. Recrystallization from ethanol rendered the title compound (m.p. 153°–154° C.).

Elemental Analysis: $C_{23}H_{33}NO$.
Calc: C, 73.47; H, 9.12; N, 3.73.
Found: C, 73.24; H, 8.87; N, 3.84.

Utilizing the above procedures, the following additional compounds were prepared.

EXAMPLE 29

N-Methyl-4-(hexyloxy)-β-phenylbenzenepropanamine

Elemental Analysis: $C_{22}H_{31}NO$.
Calc: C, 73.00; H, 8.91; N, 3.87.
Found: C, 72.82; H, 9.12; N, 3.89.
m.p. 143°–145° C.

EXAMPLE 30

N-Isopropyl-4-(hexyloxy)-β-phenylbenzenepropanamine hydrochloride

Elemental Analysis: $C_{24}H_{35}NO \cdot HCl$.
Calc: C, 73.91; H, 9.30; N, 3.59; Cl, 9.09.
Found: C, 73.62; H, 9.10; N, 3.86; Cl, 9.09.

EXAMPLE 31

N'-[3-[4-(Hexyloxy)phenyl]-2-(3,4,5-trimethoxyphenyl)-propyl]-N,N-dimethyl-1,2-ethanediamine dihydrochloride Elemental Analysis: $C_{28}H_{44}N_2O_4 \cdot 2HCl$.
Calc: C, 61.64; H, 8.50; N, 5.13; Cl, 13.00.
Found: C, 61.40; H, 8.22; N, 5.12; Cl, 13.99.
m.p. 179°–181° C.

EXAMPLE 32

β-[1,1'-Biphenyl]-4-yl-1,3-benzodioxole-5-propanamine hydrochloride

To a warmed solution of 45 g of 1,3-benzodioxole-5-aldehyde and 58 g of 4-biphenylacetonitrile in 2 liters (1) of methanol was added 100 ml of an aqueous potassium hydroxide solution (25 percent) with stirring. Within a few minutes a precipitate appeared and more methanol was added to facilitate stirring. The stirring was continued with warming and the mixture was subsequently cooled and the precipitate collected by filtration and washed with water to yield the intermediate, α-[1,3-(benzodioxole)methylene]-4-biphenylacetonitrile. The nitrile was reduced by mixing 32.5 g of said nitrile, 10 g of Raney nickel, 150 ml of anhydrous ammonia in 300 ml of ethanol which was stirred at 150° C. overnight at a pressure of 1000 psi. The catalyst and solvent were then removed and the residue was taken up in diethyl ether. Anhydrous hydrochloric acid was added to form the hydrochloride salt which was subsequently recrystallized from ethanol to yield the title compound (m.p. 192°–195° C. dec.).

Elemental Analysis: $C_{22}H_{21}NO_2 \cdot HCl$.
Calc: C, 71.83; H, 6.03; N, 3.81; Cl, 8.70.
Found: C, 71.63; H, 5.93; N, 3.79; Cl, 9.01.

EXAMPLE 33

N-Methyl-β-phenyl-1,3-benzodioxole-5-propanamine hydrochloride 150 g of 1,3-benzodioxole-5-aldehyde and 117 g of phenylacetonitrile were stirred in 1 l of methanol while 150 ml of an aqueous solution of sodium hydroxide (50 percent) was added. A precipitate formed and the resulting mixture was stirred at room temperature for an additional three hours and then filtered. The solid that was collected was recrystallized from acetone to yield α-[1,3-(benzodioxole)methylene]phenylacetonitrile. (m.p. 122°–123° C). 50 g of the nitrile was then mixed with 10 g of palladium catalyst (5 percent) and 150 ml of anhydrous methylamine in 300 ml of ethanol. The mixture was stirred at 120° C. for 12 hours at a pressure of 1500 psi. The catalyst and solvent were removed and the residue was taken up in diethyl ether and then filtered through magnesia-silica gel. The hydrochloride salt was made in the filtrate by the addition of anhydrous hydrochloric acid resulting in the title compound which was recrystallized from methanol (m.p. 223°–224° C).

Elemental Analysis: $C_{17}H_{19}NO_2 \cdot HCl$.
Calc: C, 66.77; H, 6.59; N, 4.58; Cl, 11.59.
Found: C, 66.90; H, 6.73; N, 4.81; Cl, 11.78.

Utilizing the above procedures, the following additional compounds were prepared.

EXAMPLE 34

β-Phenyl-1,3-benzodioxole-5-propanamine hydrochloride

Elemental Analysis: $C_{16}H_{17}NO_2 \cdot HCl$.
Calc: C, 65.86; H, 6.22; N, 4.80; Cl, 12.15.
Found: C, 65.67; H, 6.15; N, 4.72; Cl, 11.90.
m.p. 196°–197° C.

EXAMPLE 35

β-Phenyl-4-(trifluoromethyl)benzenepropanamine

Elemental Analysis: $C_{16}H_{16}F_3N$.
Calc: C, 60.86; H, 5.43; N, 4.44; F, 18.05.
Found: C, 61.08; H, 5.34; N, 4.33; F, 18.32.
m.p. 196°–198° C.

EXAMPLE 36

α-Methyl-4-(pentyloxy)benzenepropanamine hydrochloride 4-(4-Hydroxyphenyl)-2-butanone (49 g) was added by portions while warming to a stirred solution of potassium hydroxide (0.33 m) in 15 ml of water. To this was added dropwise, 49.8 g of 1-bromopentane and the resultant mixture was stirred at reflux temperature overnight. The mixture was allowed to cool after which 500 ml of 20% sodium hydroxide was added and the resultant mixture was stirred an additional 30 minutes followed by extraction with ethylacetate. The organic extracts were dried and evaporated to yield approximately 63 g of the desired 4-(4-pentoxyphenyl)-2-butanone which was used to prepare the title compound as follows.

23.4 g of 4-(4-pentoxyphenyl])-2-butanone (prepared as described above) and 10.7 g of benzylamine were added to 110 ml of ethanol containing 6 g of palladium catalyst (5%). The resultant mixture was stirred at 50° C. for 6 hours at a pressure of 60 psi and then stirred an additional 8 hours at room temperature. The catalyst and solvent were then removed and the residue was taken up in a volume of diethylether and then filtered through magnesia-silica gel. The diethylether was removed and the resultant residue was added to acetone and the resultant mixture was adjusted to p 2.2 with concentrated hydrochloric acid. The mixture was chilled and the pH was subsequently adjusted to 6.8 with 5N sodium hydroxide and again chilled to render the desired titled compound as a precipitate which was subsequently collected to yield the title compound (51% yield), m.p. 130°–131° C.

Elemental Analysis: $C_{15}H_{25}N$.
Calc: C, 66.28; H, 9.64; N, 5.15;
Found: C, 66.31; H, 9.67; N, 4.94.

EXAMPLE 37

4-(Cyclohexylmethoxy)-α-cyclopropylbenzenepropanamine hydrochloride

A. Preparation of 4-cyclohexylmethoxybenzaldehyde

4-Hydroxybenzaldehyde (244 g) and 354 g of cyclohexylmethylbromide were added to 1 liter of methanol containing 414 g of anhydrous potassium carbonate (3.0M). The mixture was heated to reflux temperature overnight after which it was poured into cold water and extracted with ethyl acetate. The extracts were dried and evaporated in vacuo to yield the desired subtitled intermediate.

B. Preparation of 3-[4-(cyclohexylmethoxy)phenyl]-1-cyclopropyl-2-propen-1-one 104.6 g of the compound prepared in Example 37A and 42 g of cyclopropylmethyl ketone were added to 1 liter of methanol. The resultant mixture was stirred at 10°–15° C. during the dropwise addition of 125 ml of sodium hydroxide (50%). The mixture was subsequently stirred in the cold for 2 hours to yield a solid which was collected, washed with water and then recrystallized from acetone to yield the desired subtitled intermediate,
m.p. 59°–61° C.

C. Preparation of 4-(cyclohexylmethoxy)-α-cyclopropylbenzenepropanamine 42.6 g of the ketone intermediate prepared in Example 37B and 150 ml of anhydrous ammonia were added to 285 ml of ethanol containing 15 g of a platinum sulfided catalyst (5%). The mixture was heated to 150° C. for 8 hours under an internal pressure of 1000 psi of $H_2$. The catalyst and solvent were then removed and, following distillation under reduced pressure, the desired subtitled intermediate was obtained.

D. Preparation of 4-(cyclohexylmethoxy)-α-cyclopropylbenzenepropanamine hydrochloride The intermediate of EXAMPLE 37C was taken up in diethylether and saturated with anhydrous hydrochloric acid to yield a white precipitate which was recrystallized from ethanol to yield the desired product (35% yield), m.p. 162°–164° C.

Elemental Analysis: $C_{19}H_{30}ClNO$
Calc: C, 70.45; H, 9.34; N, 4.32;
Found: C, 70.31; H, 9.13; N, 4.30.

EXAMPLE 38

4-(Cyclohexylmethoxy)-α-ethyl-N,N-dimethylbenzenepropanamine hydrochloride

A. Preparation of 1-[4-(phenylmethoxy)phenyl]-1-penten-3-one

4-Benzyloxybenzaldehyde (100 g) and 43.2 g of methylethyl ketone were added to 1.2 l of methanol and stirred at 15°–20° C. during which 125 ml of sodium hydroxide (50%) was added dropwise. Following completion of the addition of sodium hydroxide, the mixture was stirred at room temperature for about 8 hours. The resultant solid was collected and washed with water and recrystallized from acetone to yield the desired subtitled intermediate, m.p. 123°–125° C.

B. Preparation of 1-(4-hydroxyphenyl)-1-penten-3-one 90 g of the compound prepared in Example 38A was added to 900 ml of a mixture of THF and ethylacetate (2:1) and 10 g of a palladium catalyst (5%) and was maintained at room temperature overnight (pressure 60 psi of $H_2$). The catalyst and solvent were then removed to yield the desired subtitled intermediate which was used as follows without purification.

C. Preparation of 1-[4-(cyclohexylmethoxy)-phenyl]-1-penten-3-one

To 200 ml of ethanol containing 69 g of anhydrous potassium carbonate (0.5 m) was added 60.5 g of the ketone intermediate prepared in Example 38B and 63.7 g of cyclohexylmethylbromide. The resultant mixture was heated to reflux temperature overnight after which it was added to cold water and extracted with ethyl acetate. The extracts were dried and evaporated in vacuo to yield the desired subtitled intermediate.

D. Preparation of 4-(cyclohexylmethoxy)-α-ethyl-N,N-dimethylbenzenepropanamine

To 300 ml of ethanol containing 15 g of sulfided platinum catalyst (5%) was added 46.5 g of the ketone intermediate prepared in Example 38C and 150 ml of anhydrous dimethylamine. The reaction was carried out under hydrogen atmosphere at 150° C. for 12 hours at an internal pressiue of 1000 psi. After 12 hours, the catalyst and solvent were removed and, following distillation, the desired subtitled intermediate was afforded.

E. Preparation of 4-(cyclohexylmethoxy)-α-ethyl-N,N-dimethylbenzenepropanamine hydrochloride The compound prepared in Example 38D was taken up in a volume of diethylether saturated with anhydrous hydrochloric acid to render a white precipitate which was collected and recrystallized from methanol to yield the desired product (15% yield),
m.p. 142°–143° C.

Elemental Analysis: $C_{20}H_{34}ClNO$
Calc: C, 70.66; H, 10.08; N, 4.12;
Found: C, 70.25; H, 8.52; N, 4.41.

EXAMPLE 39

4-(2-Cyclohexylethoxy)-α-methyl-N-[3-(trifluoromethyl)-cyclohexyl]benzenepropanamine hydrochloride

A. Preparation of 4-]-4-(2-cyclohexylethyl)-phenyl]-2-butanone 4-(4-Hydroxyphenyl)-2-butanone (98.4 g) and 126 g of cycohexylethylbromide were added to 250 ml of ethanol containing 139 g of anhydrous potassium carbonate (1.0M). The mixture was heated to reflux temperature overnight after which it was poured into cold water and extracted with ethyl acetate. The extracts were dried and evaporated under reduced pressure to yield the desired subtitled intermediate.

B. Preparation of 3-(trifluoromethyl)cyclohexanamine 80.5 g of 3-trifluoromethylanaline was added to 200 ml of acetic acid containing 20 g of a rhodium catalyst (5%) and the resultant mixture heated for 3 hours at room temperature (60 psi). The temperature of the reaction mixture was then increased to 50° C. and maintained at that temperature for an additional 2 hours after which the catalyst was removed by filtration and the filtrate made basic with aqueous sodium hydroxide. The filtrate was subsequently extracted with ethyl acetate and the extracts dried and evaporated under reduced pressure to yield the desired subtitled intermediate.

C. Preparation of 4-(2-cyclohexylethoxy)-α-methyl-N-[3-(trifluoromethyl)cyclohexy]benzenepropanamine To 400 ml of THF containing 20 g of a 5% palladium on sulfide carbon catalyst was added 54.8 g of the ketone intermediate prepared in Example 39A and 33.4 g of the amine intermediate prepared in Example 39B. The mixture was heated to 150° C. for 8 hours under a hydrogen atmosphere (internal pressure 1000 psi) after which the catalyst and solvent were removed and distillation under reduced pressure rendered the subtitled intermediate.

D. Preparation of 4-(2-cyclohexylethoxy)-α-methyl-N-[3-(trifluoromethyl)cyclohexyl]benzenepropanamine hydrochloride.

The intermediate of Example 39C was taken up in a volume of diethylether saturated with anhydrous hydrochloric acid. A precipitate failed to form and the diethylether was evaporated and the residue was taken up in a volume of ethanol, mixed well and again evaporated to yield the residue. Acetone was added and the mixture was mixed well to render a precipitate which was collected by filtration to render a white solid as the desired product (11% yield), m.p. 191°-193° C.

Elemental Analysis: $C_{25}H_{39}ClF_3NO$.
Calc: C, 64.99; H, 8.51; N, 3.03;
Found: C, 65.02; H, 8.49; N, 3.28.

EXAMPLE 40

4-[3-[4-(Cyclohexylmethoxy)phenyl]-1-ethylpropyl]-morpholine

A. Preparation of 4-cyclohexylmethoxybenzaldehyde

To 250 ml of DMF containing about 200 g of anhydrous potassium carbonate (1.5M) was added 122 g of 4-hydroxybenzaldehyde and 177 g of cyclohexylmethylbromide. The mixture was heated to reflux temperature and maintained overnight, after which was poured into cold water and extracted with ethyl acetate. The extracts were dried and evaporated under reduced pressure to yield the desired subtitled intermediate (63% yield), b.p. 133°-138° C.

B. Preparation of 1-[4-(cyclohexylmethoxy)-phenyl]-1-penten-3-one 137.5 g of the aldehyde prepared as described in Example 40A and 144 g of methylethyl ketone were added to 1.2 L of methanol and stirred at 10°-15° C. during the dropwise addition of 200 ml of sodium hydroxide (50%). The mixture was stirred in the cold for an additional 2 hours and then at room temperature overnight to render a solid which was collected by filtration, washed with water and recrystallized from acetone to yield the desired subtitled intermediate.

C. Preparation of 4-[3-[4-(cyclohexylmethoxy)-phenyl]-1-ethylpropyl]-morpholine To 300 ml of ethanol containing 10 g of a palladium on sulfide carbon catalyst (5%) was added 40.8 g of the intermediate prepared in Example 40B and 17.4 g of morpholine. The mixture was heated to 125° C. and maintained at that temperature for 8 hours under a hydrogen atmosphere (1000 psi). The catalyst and solvent were then removed and, following distillation at reduced pressure, the desired product was afforded (65% yield), b.p. 175°-180° C.

Elemental Analysis: $C_{22}H_{35}NO_2$.
Calc: C, 76.48; H, 10.21; N, 4.05;
Found: C, 76.25; H, 10.05; N, 3.95.

EXAMPLE 41

4-Butoxy-N,N,α-trimethylbenzenepropanamine hydrochloride

A. Preparation of 4-[3-(dimethylamino)butyl]-phenol

A solution of 4-(4-hydroxyphenyl)-2-butanone (100 g) in 500 ml of ethanol with anhydrous dimethylamine (300 ml) and 5% palladium on sulfide carbon (100 g) was placed in a high pressure reaction vessel and kept under 1000 psi of $H_2$ at 175° C. for 8 hours. The resultant solution was then filtered and the solvent removed in vacuo to give an oil which was dissolved in 1N hydrochloric acid (100 ml) and extracted with two 100 ml portions of ether. The aqueous layer was adjusted to pH7 with 2N sodium hydroxide and extracted with an additional two 100 ml volumes of ether. The organic extract was retained and dried and reduced in volume to give 55 g (47% yield) of the desired subtitled intermediate.

B. Preparation of 4-butoxy-N,N,α-trimethylbenzenepropanamine hydrochloride

Potassium t-butoxide (2.34 g) was added to 3.86 g of the intermediate prepared in Example 41A in 50 ml of acetonitrile and the mixture was stirred until all of the solid had dissolved (about 10 minutes). Iodobutane (2.28 ml, 0.02 m) was added and stirring was continued for 2 hours as a precipitate formed. The solid was evaporated and the residue was dissolved in a mixture of 50 ml ether and 25 ml of 2N sodium hydroxide. The organic layer was extracted with two 25 ml portions of 1N hydrochloric acid and the acid extracts were made basic with 2N sodium hydroxide and then extracted with two 50 ml portions of ether. The ether extracts were dried and reduced in vacuo to give an oil which was converted to the hydrochloride salt as described herein and crystallized from methanol-ethyl acetate to give 2.44 g (53% yield) of the desired product, m.p. 151°–153° C.

Elemental Analysis: $C_{16}H_{28}ClNO$.
Calc: C, 67.23; H, 9.87; N, 4.90;
Found: C, 66.97; H, 9.89; N, 5.05.

EXAMPLE 42

1-[3-(4-Butoxyphenyl)-1-methylpropyl]-1H-imidazole 1-(4-Methoxyphenyl)-1-buten-3-one (10 g) in 20 ml of toluene was added dropwise to an ice bathcooled solution of sodium bis(2-methoxyethoxy)aluminum hydride (3.4M in toluene) (18.2 ml) in toluene (100 ml). The ice bath was removed and the reaction wa heated at reflux temperature for 30 minutes. After cooling to room temperature, the solution was poured into ice and excess sodium hydroxide solution and extracted with ether. The organic extract was dried and reduced in vacuo to give 9.29 g of the desired intermediate, 1-(4-methoxyphenyl)-3-hydroxybutane as an oil.

Said oil was dissolved in 100 ml of pyridine and cooled in an ice bath after which p-toluenesulfonyl chloride was added. The reaction mixture was refrigerated for 18 hours and was then poured into water and extracted with ether. The ether layer was washed with several portions of water and then dried and evaporated to give 10.31 g of the desired tosylate intermediate as an oil. The oil was immediately dissolved in 50 ml of dimethylsulfoxide along with 0.68 g of imidazole and 2.8 g of powdered potassium hydroxide. After maintaining the mixture at room temperature for 2 hours, the reaction mixture was poured into 150 m of water and extracted with three 50 m portions of ether. The ether portions were subsequently extracted with two 50 ml portions of 1N hydrochloric acid. The resultant acidic solution was made basic with 2N sodium hydroxide and extracted with two 50 ml portions of ether. The organic layers were dried and reduced in vacuo to give 1.65 g of 1-(4-methoxyphenyl)butan-3-one-imidazole as an oil.

The oil was dissolved in 48% HBr (10 ml) and heated at reflux temperature for 1 hour. The solvent was removed in vacuo and the residue was dissolved in 5N sodium hydroxide (5 ml) and extracted with three 10 ml portions of ether. The ether extracts were dried and evaporated to give 0.91 g of the desired phenol which was subsequently converted to the butyl ether by the procedure described in Example 41B which, after purification by HPLC gave 0.79 g of the desired compound as a free base oil.

$^1$NMR $(CDCl_3)\delta$ 7.56 (s,1), 7.12 (s,1), 7.00 (d,J=4.5,2), 6.96 (s,1), 6.82 (d,J=4.5,2), 4.12 (m,1), 3.94 (t,J=4.0,2), 2.51-2.32 (m,2), 2.10-1.99 (m,2), 1.80-1.70 (m,2), 1.55-1.40 (m,2), 1.47 (d,J=4.0,3), 0.97 (t,J=4.0,3).

EXAMPLE 43

4-Butoxy-N,N,N,α-tetramethylbenzenepropanaminium iodide

To an ether solution containing 1.0 g of 4-butoxy-N,N,α-trimethylbenzenepropanamine (the free base of the compound prepared in Example 41B) was added 2.5 ml of iodomethane and, over a period of 4 hours an oil separated from the solution. The solvent was evaporated and the residue was crystallized from ethyl acetate to give 0.48 g (31% yield) of the desired titled compound, m.p. 160°–165° C.

Elemental Analysis: $C_{17}H_{30}INO$.

Calc: C, 52.18; H, 7.73; N, 3.58;
Found: C, 51.92; H, 7.53; N, 3.30.

Utilizing the procedures set forth herein, the following additional compounds were prepared.

EXAMPLE 44

N-Ethyl-N'-[1-[2-[4-(hexyloxy)phenyl]ethyl]heptyl]-1,2-ethanediamine dihydrochloride, m.p. 103°–105° C.

Elemental Analysis: $C_{25}H_{43}Cl_2N_2O$.
Calc: C, 64.77; H, 10.44; N, 6.04;
Found: C, 64.50; H, 10.19; N, 6.29.

EXAMPLE 45

N,N-Dimethyl-N'[1-methyl-3-[4-(tetradecyloxy)-phenyl]-propyl]-1,2-ethanediamine dihydrochloride, m.p. 198° C. (dec.)

Elemental Analysis: $C_{28}H_{54}Cl_2N_2O$.
Calc: C, 66.51; H, 10.76; N, 5.54;
Found: C, 66.29; H, 11.05; N, 5.43.

EXAMPLE 46

N'-[3-[4-(2-Cyclohexylethoxy)phenyl]-1-methylpropyl]-N,N-dimethyl-1,2-ethanediamine dihydrochloride, m.p. 192°–194° C.

Elemental Analysis: $C_{22}H_{40}Cl_2N_2O$
Calc: C, 62.99; H, 9.61; N, 6.68;
Found: C, 63.16; H, 9.81; N, 6.59.

EXAMPLE 47

N-[3-[4-(Cyclopentyloxy)phenyl]-1-methylpropyl]-4-morpholineethanamine dihydrochloride, m.p. 203°–205° C.

Elemental Analysis: $C_{21}H_{36}Cl_2N_2O_2$.
Calc: C, 60.14; H, 8.65; N, 6.68;
Found: C, 60.01; H, 8.47; N, 6.69.

EXAMPLE 48

4-(Cyclohexylmethoxy)-α-(2-methylpropyl)benzenepropanamine hydrochloride, m.p. 189°–190° C.

Elemental Analysis: $C_{20}H_{34}ClNO$.
Calc: C, 70.66; H, 10.08; N, 4.12;
Found: C, 70.90; H, 9.81; N, 3.89.

EXAMPLE 49

N'-[3-[4-(Heptyloxy)phenyl]-1-methylpropyl]-N,N-dimethyl-1,2-ethanediamine dihydrochloride, m.p. 199°–200° C.

Elemental Analysis: $C_{21}H_{40}Cl_2N_2O$.
Calc: C, 61.90; H, 9.90; N, 6.88;
Found: C, 61.63; H, 9.61; N, 7.01.

EXAMPLE 50

4-(Decyloxy)-α-methylbenzenepropanamine hydrochloride, m.p. 112° C. (dec.)

Elemental Analysis: $C_{20}H_{36}ClNO$.
Calc: C, 70.25; H, 10.61; N, 4.10;
Found: C, 70.43; H, 10.57; N, 4.36.

EXAMPLE 51

4-(Heptyloxy)-α-methylbenzenepropanamine hydrochloride, m.p. 122°–124° C.

Elemental Analysis: $C_{17}H_{30}ClNO$.
Calc: C, 68.09; H, 10.08; N, 4.67;
Found: C, 68.38; H, 9.80; N, 4.42.

EXAMPLE 52

N'-[3-[4-(Dodecyloxy)phenyl]-1-methylpropyl]-N,N-dimethyl-1,2-ethanediamine dihydrochloride, m.p. 192° C. (dec.)

Elemental Analysis: $C_{26}H_{50}Cl_2N_2O$.
Calc: C, 65.39; H, 10.55; N, 5.87;
Found: C, 65.21; H, 10.48; N, 6.66.

EXAMPLE 53

N-[1-Methyl-3-[4-(nonyloxy)phenyl]propyl]-4-morpholineethanamine dihydrochloride, m.p. 203°–205° C.

Elemental Analysis: $C_{25}H_{46}Cl_2N_2O_2$.
Calc: C, 62.88; H, 9.71; N, 5.87;
Found: C, 62.91; H, 9.91; N, 5.76.

EXAMPLE 54

N,N-Dimethyl-N'-[1-methyl-3-[4-(nonyloxy)phenyl]propyl]-1,2-ethanediamine dihydrochloride, m.p. 221° C. (dec.).

Elemental Analysis: $C_{23}H_{44}Cl_2N_2O$.
Calc: C, 63.43; H, 10.18; N, 6.43;
Found: C, 63.44; H, 10.26; N, 6.18.

EXAMPLE 55

N,N,α-Trimethyl-4-(1-methylethoxy)benzenepropanamine hydrobromide, m.p. 143°–146° C.

Elemental Analysis: $C_{15}H_{26}BrNO$.
Calc: C, 56.76; H, 8.29; N, 4.43;
Found: C, 56.94; H, 8.44; N, 4.52.

EXAMPLE 56

4-(2-Butenyloxy)-N,N,α-trimethylbenzenepropanamine hydrochloride, m.p. 127°–136° C.

Elemental Analysis: $C_{16}H_2ClNO$.
Calc: C, 67.71; H, 9.23; N, 4.93;
Found: C, 67.45; H, 9.22; N, 4.97.

EXAMPLE 57

4-(2-Methylthioethoxy)-N,N,α-trimethylbenzenepropanamine hydrochloride, m.p. 114°–115° C.

Elemental Analysis: $C_{15}H_{26}ClNOS$.
Calc: C, 59.29; H, 8.62; N, 4.61;
Found: C, 59.07; H, 8.49; N, 4.58.

EXAMPLE 58

4-[2-(Dimethylamino)ethoxy]-N,N,α-trimethylbenzenepropylamine dihydrochloride, m.p. 245°–248° C.

Elemental Analysis: $C_{16}H_{30}Cl_2N_2O$.
Calc: C, 56.97; H, 8.96; N, 8.30;
Found: C, 57.10; H, 8.69; N, 8.54.

EXAMPLE 59

4-8 4-[3-(Dimethylamino)butyl]phenoxy]butanenitrile hydrochloride, m.p. 123°–126° C.

Elemental Analysis: $C_{16}H_{25}ClN_2O$.
Calc: C, 64.74; H, 8.49; N, 9.44;
Found: C, 64.48; H, 8.42; N, 9.46.

EXAMPLE 60

3,3-Dimethyl-1-[4-[3-(dimethylamino)-1-butyl]phenoxy]-2-butenone hydrochloride, m.p. 161°–165° C.

Elemental Analysis: $C_{18}H_{30}ClNO_2$.
Calc: C, 65.94; H, 9.22; N, 4.27;
Found: C, 65.73; H, 9.22; N, 4.46.

EXAMPLE 61

N,N,α-Trimethyl-4-[2-(1H-imidazol-1-yl)ethoxy]benzenepropanamine, oil.

EXAMPLE 62

N,N,α-Trimethyl-4-[2-(1H-1,2,4-triazol-1-yl)ethoxy]-benzenepropanamine, oil.

EXAMPLE 63

N,N,α-Trimethyl-4-[(3-fluorophenyl)methoxy]benzenepropanamine hydrochloride, m.p. 150°–152° C.

Elemental Analysis: $C_{19}H_{25}ClFNO$.
Calc: C, 67.54; H, 7.46; N, 4.15;
Found: C, 67.58; H, 7.57; N, 4.18.

EXAMPLE 64

N,N,α-Trimethyl-4-[(2,4-dichlorophenyl)methoxy]benzenepropanamine hydrochloride, m.p. 147°–149° C.

Elemental Analysis: $C_{19}H_{24}Cl_3NO$.
Calc: C, 58.70; H, 6.22; N, 3.60;
Found: C, 58.94; H, 6.13; N, 3.56.

EXAMPLE 65

N,N,α-Trimethyl-4-[[4-(trifluoromethyl)phenyl]methoxy]-benzenepropanamine hydrochloride, m.p. 158°–161° C.

Elemental Analysis: $C_{20}H_{25}ClF_3NO$.
Calc: 61.93; H, 6.50; N, 3.61;
Found: C, 62.00; H, 6.43; N, 3.67.

EXAMPLE 66

Benzenesulfonic acid 4-[3-(dimethylamino)butyl]phenylester, oil.

Elemental Analysis: $C_{18}H_{23}NO_3S$.
Calc: C, 64.84; H, 6.95; N, 4.20;
Found: C, 64.84; H, 7.03; N, 4.46.

EXAMPLE 67

Propane sulfonic acid 4-3-(dimethylamino)butyl]phenylester, oil

Elemental Analysis: $C_{15}H_{25}NO_3S$.
Calc: C, 60.17; H, 8.42; N, 4.68;
Found: C, 59.98; H, 8.33; N, 4.65.

EXAMPLE 68

4-Butoxy-N-ethyl-N,α-dimethylbenzenepropanamine hydrochloride, m.p. 93°–95° C.

Elemental Analysis: $C_{17}H_{30}ClNO$.
Calc: C, 68.09; H, 10.08; N, 4.67;
Found: C, 68.02; H, 10.07; N, 4.44.

EXAMPLE 69

4-[3-(4-Butoxyphenyl)-1-methylpropyl]-2,6-dimethylmorpholine hydrochloride, m.p. 151°–153° C.

Elemental Analysis: $C_{20}H_{34}ClNO_2$.
Calc: C, 67.49; H, 9.63; N, 3.94;
Found: C, 67.23; H, 9.76; N, 3.87.

EXAMPLE 70

4-Butoxy-α-ethyl-N,N-dimethylbenzenepropanamine hydrochloride, m.p. 84°–86° C.

Elemental Analysis: $C_{17}H_{30}ClNO$.
Calc: C, 68.09; H, 10.08; N, 4.67;

Found: C, 67.82; H, 9.99; N, 4.70.

EXAMPLE 71

3-(Cyclohexylmethoxy)-4-methoxy-α-methyl-β-phenylbenzenepropanamine hydrochloride

A. Preparation of 3-cyclohexylmethoxy-4-methoxybenzaldehyde

In 175 ml of DMF containing 138 g of anhydrous potassium carbonate (1.0 m) was added 100 g of 3-hydroxy-4-methoxybenzaldehyde and 127 g of cyclohexylmethybromide. The mixture was heated at reflux temperature overnight and then poured into cold water and extracted with ethyl acetate. The extracts were dried and evaporated in vacuo to render the desired subtitled intermediate, b.p. 130°-135 ° C.

B. Preparation of 4-[3-(cyclohexylmethoxy)-4-methoxyphenyl]-3-phenyl-3-buten-2-one 100.1 g of the aldehyde prepared in Example 71A and 53.6 g of 3-phenyl-2-propanone and 5 ml of piperidine were added to 100 ml of toluene and the resultant mixture heated at reflux temperature for 4 hours. The solvent was removed in vacuo to yield the desired subtitled intermediate (90% yield).

C. Preparation of 3-(cyclohexylmethoxy)-4-methoxy-α-methyl-β-phenylbenzenepropanamine 36.4 g of the compound prepared by Example 71B and 75 ml of anhydrous ammonia were added to 150 ml of ethanol containing 7 g of a 5% palladium on sulfide carbon catalyst. The mixture was heated to 125° C. and maintained for 8 hours under 1000 psi of hydrogen. After 8 hours the catalyst and solvent were removed in vacuo to yield the desired subtitled product (51% yield), b.p. 190°-195° C.

D. Preparation of 3-(cyclohexylmethoxy)-4-methoxy-α-methyl-β-phenylbenzenepropanamine hydrochloride 14.7 g of the intermediate product prepared in Example 71C was taken up in diethylether, saturated with anhydrous hydrochloric acid. The resultant precipitate was collected and recrystallized from ethanol to yield the desired titled product (30% yield), m.p. 173°-175° C.

Elemental Analysis: $C_{24}H_{34}ClNO_2$.
Calc: C, 71.35; H, 8.48; N, 3.47;
Found: C, 71.65; H, 8.68; N, 3.69.

EXAMPLE 72

4-(Hexyloxy)-β-4-methoxyphenyl-αmethylbenzenepropanamine hydrochloride

A. Preparation of hexyloxybenzaldehyde

To 250 ml of DMF containing 207 g of anhydrous potassium carbonate (1.5M) was added 122 g of 4-hydroxybenzaldehyde and 181.6 g of hexylbromide. The resultant mixture was heated at reflux temperature overnight after which it was poured into cold water and extracted with ethylacetate. The extracts were dried and evaporated in vacuo to afford the desired subtitled intermediate (80% yield), b.p. 110°-115° C.

B. Preparation of 4-[4-(hexyloxy)phenyl]-3-(4-methoxyphenyl)-2-butanone 49.2 g of 3-(4-methoxyphenyl)-2-propanone and 61.8 g of 4-hexyloxybenzaldehyde were added to 100 ml of toluene containing 4 ml of piperidine. The resultant mixture was heated at reflux temperature overnight after which the solvent was removed in vacuo to afford the desired subtitled intermediate (46% yield), b.p. 230°-235° C.

C. Preparation of 4-(hexyloxy)-β-(4-methoxyphenyl)-α-methylbenzenepropanamine To 300 ml of ethanol containing 9 g of a 5% palladium on sulfide carbon catalyst was added 44 g of the intermediate ketone prepared by Example 72B and 150 ml of anhydrous ammonia. The resultant mixture was heated to 125° C. for 8 hours under 1000 psi of $H_2$. At the end of 8 hours, the catalyst and solvent were removed in vacuo to yield the desired subtitled intermediate (73% yield), b.p. 190°-195° C.

D. Preparation of 4-(hexyloxy)-β-(4-methoxyphenyl)-α-methylbenzenepropanamine hydrochloride 21.9 g of the intermediate prepared in Example 72C was added to a volume of diethylether containing anhydrous hydrochloric acid. A precipitate formed which was collected and recrystallized from ethanol to render the desired titled product (61% yield), m.p. 146°-148° C.

Elemental Analysis: $C_{23}H_{34}ClNO_2$.
Calc: C, 70.48; H, 8.74; N, 3.57;
Found: C, 70.67; H, 8.82; N, 3.37.

Utilizing the procedures set forth herein, the following additional compounds were prepared.

EXAMPLE 73

4-(2-Ethoxy)-α-methyl-β-phenylbenzenepropanamine hydrochloride, m.p. 236°-238° C.

Elemental Analysis: $C_{20}H_{28}ClNO_2$.
Calc: C, 68.65; H, 8.07; N, 4.00;
Found: C, 68.45; H, 7.99; N, 3.86.

EXAMPLE 74

4-(Butoxy-N,Nα,β-tetramethylbenzenepropanamine hydrochloride, m.p. 130°-132° C.

Elemental Analysis: $C_{17}H_{30}ClNO$.
Calc: C, 68.09; H, 10.08; N, 4.67;
Found: C, 68.14; H, 10.31; N, 4.85.

EXAMPLE 75

4-(3,3-Dimethylbutoxy)-N,N,α trimethylbenzene-propanamine hydrochloride, m.p. 175°-178° C.

EXAMPLE 76

4-(2-Methoxyethoxy)-N,N,α-trimethylbenzene-propanamine hydrochloride, m.p. 110°-113° C.

EXAMPLE 77

1-[3-[4-(Butoxy)phenyl]-1-methylpropyl]-pyrrolidine hydrochloride, m.p. 141°-143° C.

EXAMPLE 78

4-Butoxy-N,N,β-trimethylbenzenepropanamine hydrochloride, m.p. 146°-149° C.

EXAMPLE 79

4-(3,3-Dimethylbutoxy)-N,N,α-trimethylbenzene-propanamine hydrochloride, m.p. 150°-153° C.

EXAMPLE 80

4-Cyclopentylmethoxy-N,N-α-trimethylbenzene-propanamine hydrochloride, m.p. 178°-180° C.

EXAMPLE 81

4-Cyclopentylmethoxy-N,N-α-trimethylbenzene-propanamine, m.p. 170°-172° C.

EXAMPLE 82

4-[(4-Fluorophenyl)methoxy]-N,N,α-trimethylbenzene-propanamine hydrochloride, m.p. 150°-152° C.

EXAMPLE 83

4-(1,1-Dimethylethyl)-N,N,α-trimethylbenzene-propanamine hydrochloride, m.p. 190°-193° C.

EXAMPLE 84

N,N,α-Trimethyl-4-(phenylmethoxy)benzene propanamine hydrochloride, m.p. 138°-142° C.

As previously mentioned, the compounds of the present invention are anticoagulant agents, antifungal agents, or both. Anticoagulant agents find utility in the treatment of, for example, venous thrombosis and thromboembolic disease, arterial thrombosis and thromboembolic disease, myocardial infarctions, pulmonary embolism, cerebrovascular disease, thrombotic occlusions during and subsequent to thrombolytic therapy or angioplastic therapy and, in general, any other such conditions for which anticoagulant therapy is indicated. Such conditions include but are not limited to, thrombotic complications of other diseases, for example, cancer, tumor metastasis, diabetes, chronic inflammation, sepsis, shock and other conditions where preventative or prophylactic anticoagulant effects are desired. Additionally, compounds of the present invention act as antithrombotic agents. For these purposes, an effective anticoagulant amount of a compound of the present invention or a pharmaceutically acceptable salt thereof is administered to a patient in need thereof. By "effective anticoagulant amount" is meant that quantity of one or more compounds of the present invention (or a pharmaceutically acceptable salt or salts thereof) sufficient to alleviate the condition for which it is being administered. Typically, this amount will range from about 0.5 milligrams per kilogram (mg/kg) per day to about 100 mg/kg per day in singe or divided doses. Preferably, this amount will range from about 0.5 mg/kg per day to about 25 mg/kg per day.

Similarly, as antifungal agents an effective antifungal amount of a compound of the present invention or a pharmaceutically acceptable salt thereof is administered to a patient in need thereof. By "effective antifungal amount" is meant that quantity of one or more compounds of the present invention (or a pharmaceutically acceptable salt or salts thereof) sufficient to alleviate the condition for which it is being administered. Typically, this amount will range from about 0.5 mg/kg per day to about 100 mg/kg per day in single or divided doses. Preferably, this amount will range from about 0.5 mg/kg per day to about 25 mg/kg per day. However, it will be understood that the amount of the compound to be administered either as an anticoagulant or antifungal agent will be determined by a physician in light of the relevant circumstances including the condition being treated, the age, weight and response of the patient, the route of administration and the like. Accordingly, the above dosage ranges are not to be construed as a limitation on the scope of the invention in any way.

The compounds of the present invention or pharmaceutically acceptable salts thereof are administered via anticoagulant or antifungal pharmaceutical compositions. Such compositions contain, in admixture with one or more pharmaceutically acceptable carriers, sufficient amounts of one or more of the compounds of the present invention or pharmaceutically acceptable salts thereof to deliver an effective anticoagulant or antifungal amount of said compound(s) to a patient for whom such therapy is administered. The choice of pharmaceutically acceptable carriers will be dictated by the route of administration selected. For example, preferably said compounds are administered orally as by means of tablets, capsules, powders, suspensions, solutions, syrups and the like, including sustained release preparations thereof. Accordingly, such compositions utilize pharmaceutically acceptable carriers containing materials such as diluents, binders, lubricants, disintegrators, buffering agents, surfactants, emulsifying agents, dispersants, flavoring agents and the like. Further, dosage forms for parenteral administration can also be prepared by suspending or dissolving a quantity of a compound of the present invention (or a pharmaceutically acceptable salt thereof) in a non-toxic liquid pharmaceutically acceptable carrier suitable for injection such as an aqueous or oleaginous medium and sterilizing the suspension or solution. Alternatively, a measured amount of said compound may be placed in a vial and the vial and its contents sterilized and sealed. An accompanying vial may then be provided which contains the carrier for purposes of mixing prior to administration. Such parenteral compositions employ pharmaceutically acceptable carriers such as water for injection, bacteriostatic water for injection, sesame oil, groundnut oil, aqueous propylene glycol, N,N'-dimethylformamide, and the like. Other appropriate pharmaceutical compositions may be readily prepared by the skilled artisan depending on the specific route of administration selected. Further information pertinent to the preparation of such compositions may be obtained by reference to standard treatises such as Remington's Pharmaceutical Sciences, Seventeenth Edition, Mack Publishing Company, Easton, Pa. (1985), which is incorporated herein by reference.

The anticoagulant activity of the compounds of the present invention was demonstrated by a prothrombin time test which was measured as a function of thromboplastin clotting time in human plasma. Briefly, to 0.1 ml of each of human plasma, normal saline and thromboplastin was added 0.03 ml of the test compound of the present invention (2 mg/ml in 50 percent methanol). The clotting time was measured at 37° C. with a Fibrometer. The results of this study are shown in Table I.

TABLE 1

PLASMA PROTHROMBIN TIMES[a]

| Compound Example No. | Concentration[b] | | | | |
|---|---|---|---|---|---|
| | 180 | 90 | 45 | 22 | 11 | 0 |
| 1 | >300 | >300 | 91 | 43 | 32 | 21 |
| 2 | >300 | >300 | 79 | 38 | — | 21 |
| 4 | >300 | 91 | 37 | — | — | 21 |
| 5 | 190 | 53 | 25 | — | — | 21 |
| 6 | 83 | 46 | 26 | 20 | — | 20 |
| 7 | >300 | 200 | 36 | 25 | — | 21 |
| 8 | 130 | 45 | 23 | — | — | 21 |
| 9 | 25 | — | — | — | — | 21 |
| 10 | 60 | — | — | — | — | 21 |
| 11 | 20 | — | — | — | — | 19 |
| 12 | 75 | 33 | 21 | — | — | 19 |
| 13 | 200 | — | — | — | — | 21 |
| 14 | 101 | — | — | — | — | 21 |
| 15 | 80 | 30 | 21 | — | — | 21 |
| 16 | 235 | 81 | 57 | 27 | — | 20 |
| 17 | 240 | 81 | 48 | 21 | — | 21 |
| 18 | 125 | — | — | — | — | 21 |
| 19 | 174 | — | — | — | — | 16 |
| 20 | >200 | 74 | 36 | — | — | 22 |
| 22 | >300 | — | — | — | — | 21 |
| 23 | 101 | — | — | — | — | 22 |
| 24 | 48 | 28 | 22 | — | — | 22 |
| 25 | 50 | 29 | 22 | — | — | 22 |
| 26 | 500 | 67 | 29 | — | — | 22 |
| 27 | 100 | — | — | — | — | 23 |
| 28 | 110 | 35 | 23 | 17 | — | 16 |
| 29 | 87 | 31 | 17 | — | — | 16 |
| 30 | 69 | — | — | — | — | 17 |
| 31 | 150 | — | — | — | — | 19 |
| 32 | 222 | 66 | 27 | | | 21 |
| 33 | 18 | — | — | — | — | 18 |
| 34 | 21 | — | — | — | | 21 |
| 35 | 68 | — | — | — | — | 17 |
| 36 | 170 | 41 | 24 | — | — | 17 |
| 37 | — | — | — | — | 22 | 20 |
| 38 | — | — | — | — | 22 | 21 |
| 39 | — | — | 90 | — | — | 20 |
| 41 | 41 | 24 | 21 | — | — | — |
| 44 | 300 | — | 33 | 25 | 22 | 20 |
| 49 | 260 | 167 | 36 | 34 | 22 | 20 |
| 50 | 100 | 36 | 21 | — | — | 17 |
| 51 | >300 | 52 | 25 | — | — | 17 |
| 52 | 87 | 20 | — | — | — | 20 |
| 53 | 240 | 53 | 23 | — | — | 20 |
| 54 | >300 | 99 | 37 | — | — | 16 |
| 75 | 90 | 52 | 32 | 23 | 18 | |
| 76 | 18 | 17 | 17 | — | — | |
| 77 | 53 | 24 | 23 | 16 | 15 | |
| 78 | 67 | 31 | 23 | — | — | |
| 79 | 90 | 55 | 31 | 21 | 19 | |
| 80 | 88 | 43 | 24 | 19 | 17 | |
| 81 | 47 | 25 | 20 | — | — | |
| 82 | 75 | 29 | 24 | 19 | 18 | |
| 83 | 37 | 26 | 21 | — | — | |

[a]Expressed in seconds
[b]Concentration of compound tested in micrograms per milliliter of plasma The compound of Example 3 when tested at a concentration of 139, 69, 28 and 0 micrograms per ml exhibited prothrombin times of 80, 25, 16 and 15 seconds, respectively. The compound of Example 21 is insoluble in methanol and therefore a prothrombin time was not determined.

As noted previously, some of the compounds of the present invention also exhibit in vitro antifungal activity. The antifungal activity was assayed in vitro against *Candida abicans* A26, *Trichophyton mentagrophytes* CDC27, and *Aspergillus flavus* M152. The inocula, previously frozen under liquid nitrogen in a lactose, glycerol and water solution, were standardized by counting spores with a hemocytometer. Final concentrations (*C. albicans*, 1×10⁵ cells/m; *T. mentagrophytes*, 1×10⁶ cells/ml; *A. flavus*, 1×10⁵ cells/ml) in RPMI 1640 plus 10% fetal calf serum were added to each of the 96 wells of a microtiter plate (100 µl/well). The compounds to be tested were solubilized in either water or ethanol and added to the microtiter wells in serial dilutions to give final concentrations in the range 0.039–20 µg/ml. The plates were incubated at 35° C. for 48 hours. The minimum inhibitory concentration (MIC) values were determined as the highest dilution showing 95–100% inhibition of growth. The results of this study are shown in Table 2.

TABLE 2

IN VITRO ANTIFUNGAL ACTIVITY[a]

| Compound Example No. | C.a.[b] | A.f.[c] | T.m.[d] |
|---|---|---|---|
| 1 | 10 | 10 | 10 |
| 2 | 20 | 10 | 20 |
| 4 | 10 | 5 | 5 |
| 6 | 10 | 5 | 5 |
| 16 | 20 | 10 | 10 |
| 22 | 20 | 10 | 10 |
| 26 | 10 | 5 | 10 |
| 39 | 5 | >20 | >20 |
| 41 | 0.156 | 1.25 | 0.078 |
| 46 | 10 | 20 | 10 |
| 47 | 10 | 10 | 20 |
| 55 | 2.5 | 10 | 2.5 |
| 56 | 0.625 | 5 | 0.312 |
| 57 | 1.25 | 20 | 0.312 |
| 58 | 1.25 | 20 | 10 |
| 59 | 2.5 | 20 | 20 |
| 60 | 10 | 10 | 0.625 |
| 61 | 5 | >20 | 10 |
| 62 | 10 | 20 | 10 |
| 63 | 0.625 | 5 | 1.25 |
| 64 | 20 | 5 | 5 |
| 65 | 20 | 10 | 5 |
| 66 | 10 | 20 | 5 |
| 67 | 20 | 20 | >20 |
| 68 | 0.625 | 0.625 | 1.25 |
| 69 | >20 | >20 | 1.25 |
| 70 | 0.156 | 10 | 0.156 |
| 71 | 20 | 10 | 10 |
| 72 | 10 | 10 | 5 |
| 84 | 0.156 | 10 | 0.312 |

[a]Minimum inhibitory concentration expressed in µg/ml
[b]C.a. means *Candida albicans* A26
[c]A.f. means *Aspergillus flavus* M152
[d]T.m. means *Trichophyton mentagrophytes* CDC27

We claim:

1. A method of inhibiting the coagulation of blood in a patient in need thereof comprising administering to said patient an effective anticoagulant amount of a compound of the formula

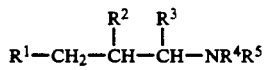

wherein $R^1$ is

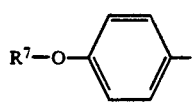

wherein $R^7$ is $C_1$–$C_{14}$ alkyl or -$(CH_2)_n$Z, wherein n is an integer from 1–4, both inclusive and Z is phenyl; $R^2$ is hydrogen, phenyl or naphthyl; and $R^3$, $R^4$ and $R^5$ are each independently hydrogen or $C_1$–$C_4$ alkyl, and pharmaceutically acceptable salts thereof.

2. The method of claim 1 where, in the definition of $R^1$, the value $R^7$ is $C_3$–$C_{10}$ alkyl or, when $R^7$ is —$(CH_2)_nZ$, n is 1 or 2; $R_2$ is hydrogen or phenyl; and $R^3$, $R^4$ and $R^5$ are each independently hydrogen or $C_1$–$C_4$ alkyl; and pharmaceutically acceptable salts thereof.

3. The method of claim 1 where, in the definition of $R^1$, the value $R^7$ is $C_4$–$C_7$ alkyl and pharmaceutically acceptable salts thereof.

4. The method of claim 3 wherein the compound employed is α-methyl-4-(pentyloxy)benzenepropanamine hydrochloride.

5. The method of claim 3 wherein the compound employed is 4-(heptyloxy)-α-methylbenzenepropanamine hydrochloride.

6. The method of claim 3 wherein the compound employed is 4-(hexyloxy)-β-phenylbenzenepropanamine hydrochloride.

7. The method of claim 3 wherein the compound employed is 4-butoxy-N,N,α-trimethylbenzenepropanamine hydrochloride.

* * * * *